(12) United States Patent
Pang

(10) Patent No.: US 6,179,421 B1
(45) Date of Patent: Jan. 30, 2001

(54) OCULAR MICROCIRCULATION EXAMINATION AND TREATMENT APPARATUS

(75) Inventor: Kian Tiong Pang, Singapore (SG)

(73) Assignee: Avimo Group Limited, Singapore (SG)

(*) Notice: Under 35 U.S.C. 154(b), the term of this patent shall be extended for 0 days.

(21) Appl. No.: 09/419,807

(22) Filed: Oct. 18, 1999

Related U.S. Application Data

(63) Continuation of application No. PCT/GB98/01131, filed on Apr. 17, 1998.

(30) Foreign Application Priority Data

Apr. 17, 1997 (GB) .................................................. 9707809
Mar. 2, 1998 (GB) .................................................. 9804420

(51) Int. Cl.$^7$ ................................................. A61B 3/10
(52) U.S. Cl. ........................................................ 351/205
(58) Field of Search ................................... 351/205, 206, 351/245, 246, 221, 213; 396/18

(56) References Cited

U.S. PATENT DOCUMENTS

| 4,838,679 | 6/1989 | Bille | 351/205 |
|---|---|---|---|
| 5,090,416 | 2/1992 | Ogino et al. | 128/691 |
| 5,321,446 | 6/1994 | Massig et al. | 351/214 |
| 5,394,199 | 2/1995 | Flower | 351/206 |
| 5,630,179 | * 5/1997 | Kishida | 351/206 |
| 5,914,770 | * 6/1999 | Bergner et al. | 351/206 |

FOREIGN PATENT DOCUMENTS

| 39 26 652 A1 | 4/1991 | (DE) . |
|---|---|---|
| 42 05 865 A1 | 9/1993 | (DE) . |
| 0 167 877 | 1/1986 | (EP) . |
| 0 284 248 | 9/1988 | (EP) . |

* cited by examiner

*Primary Examiner*—George Manuel
(74) *Attorney, Agent, or Firm*—Sterne, Kessler, Goldstein & Fox, p.l.l.c.

(57) ABSTRACT

Ophthalmologic examination apparatus comprises a light source, illumination means for directing light from the source along an illumination path and into the fundus of an eye of a patient, imaging means for directing fluorescence from the fundus of the patient along an imaging path to enable an image of the eye to be viewed, wherein the illumination and imaging paths are arranged as a confocal microscope adapted to focus on the fundus of the eye. A method of diagnosis of disease in an eye of a patient comprises providing in the ocular circulation of the patient: a first dye which fluoresces in response to illumination at a first predetermined wavelength; and a second dye which fluoresces in response to illumination at a second predetermined wavelength; wherein the first and second dyes fluoresce at different wavelengths; illuminating the fundus of the patient so as to excite the first dye at the first predetermined wavelength, and viewing an image of the eye by viewing fluorescence from the first dye; and subsequently illuminating the fundus of the patient so as to excite the second dye at the second predetermined wavelength, and viewing an image of the eye by viewing fluorescence from the second dye.

45 Claims, 6 Drawing Sheets

OMVAT

OCULAR MICROCIRCULATION EXAMINATION AND TREATMENT APPARATUS

RELATED APPLICATION

This application is a continuation of International Appl No. PCT/GB98/01131, filed Apr. 17, 1998.

BACKGROUND OF THE INVENTION

1. Field of the Invention

This invention relates to method and apparatus for examination of ocular microcirculation and subsequent treatment to prevent, ameliorate or inhibit worsening of disease associated with abnormalities of choroidal and/or subretinal microcirculation. In particular, the invention relates to method and apparatus for diagnosis and treatment of ocular neovascularization.

2. Related Art

A pathology of current interest is age-related macular degeneration, symptoms of which include the growth of fibrovascular membranes and new blood vessels around, and from the choroid below, the macula. The prognosis is progression to eventual blindness in the aged population with this illness. The choroid is the layer below the Bruch's membrane and the retinal pigment epithelium. The neovascularization typical of this disease arises from the capillary network (called the choriocapillaris) which, for our intents and purposes, may be considered as flat in the microscopic field of view or region of interest. Diabetic retinopathy is another disease associated with neovascularization in the retina.

The progression of these diseases includes the growth of new blood vessels in the choroid and the retina. This neovascularization can occur in different layers in the fundus and may lead to blindness. These new, microscopic vessels are fragile. They may push upwards, off the plane of the normally flat choroidal capillary networks, into or against the retina (in which the light-sensing ganglion cells reside) or the Bruch's membrane or the retinal pigment epithelium, resulting in bleeding, and/or retinal detachment which may lead to blindness.

Current techniques for examining such diseases include fluorescein angiography (SF) and indocyanine green angiography (ICG). These techniques do not resolve the microscopic details which permit the earliest possible detection of the existence and the exact locations of these new vessels. The ophthalmologist requires angiographs, then time to study them, deciding on suspect areas, whether to recall the patient for confirmatory angiographs or for treatment. Also, even if visible damage is noted, separate techniques (eg laser photocoagulation) using different instruments, must then be employed for later treatment. There is therefore a delay from examination to treatment, causing inconvenience to the patient in the multiple visits required. The additional costs in the different instruments and the manpower for handling these different instruments as well as the multiple visits are disadvantages.

There are several different techniques for locating neovascularization. Some of them are still experimental or undergoing clinical trials, (eg Optical Coherence Tomography—OCT). The existing commercial devices do not provide high-resolution and/or high-magnification images. Some simply take electronic pictures of the entire fundus (at low magnification), using false colour and other image-processing means to enhance the low resolution images.

The current treatment techniques for the removal of neovascularization employ imprecise local areal destruction (usually using a laser beam) after damage becomes visible; damage is significant if it is visible even in low-magnification, low-resolution angiographs. The laser destroys the suspect neovascularization by destroying and coagulating the area surrounding the suspect neovascularization location. Other means, some still experimental, of terminating neovascularization involve invasive methods like optic fibre insertion into the vitreous chamber.

U.S. Pat. No. 4,838,679 describes an apparatus for and a method of examining the front parts of human eyes. The apparatus is specifically designed for corneal examination using light reflected from a raster-scanning laser source. The apparatus is not suitable for fundus examination and does not describe treatment of neovascularization.

U.S. Pat. No. 4,213,678 describes an apparatus for examining the fundus. Again, this is achieved using reflected light and via scanning with a laser source of light. Resolution achieved with this apparatus is not sufficient for early diagnosis of neovascularization. There is reference to treatment of the fundus using a laser but no details are provided.

Currently, no known apparatus enables examination of those parts of the eye at the macula or in the layers below it with sufficient image quality for neovascularization to be detected before visible macula damage occurs, or enables examination of those parts of the eye at or around the fovea with sufficient data for detection of feeder vessels of a neovascular net.

Further, no apparatus is known that enables early diagnosis of macular degeneration and its treatment prior to significant loss of vision.

SUMMARY OF THE INVENTION

It is an object of this invention to provide method and apparatus to view, analyze, and treat certain diseases of the fundus of the eye. More specifically, an object of at least the preferred embodiments of the invention is to view, analyze and treat choroidal/subretinal and/or retinal neovascularization, especially as seen in age-related macular degeneration and diabetic retinopathy. An associated object is to provide method and apparatus for detailed observation of the microcirculation in the fundus of the eye. A further object is to provide method and apparatus for tracking the movement of individual blood cells and plasma in the retinal and optic disc microcirculation. A yet further object includes the provision of method and apparatus for examination of the microcirculation of the eye using two or more dyes.

Accordingly, a first aspect of the invention provides ophthalmologic examination apparatus comprising:
   a light source;
   illumination means for directing light from the source along an illumination path and into the fundus of an eye of a patient;
   imaging means for directing fluorescence from the fundus of the patient along an imaging path to enable an image of the eye to be viewed;
   wherein the illumination and imaging paths are arranged as a confocal microscope adapted to focus on the fundus of the eye.

In the present invention, the term "confocal" in relation to microscopy is used to indicate a confocal arrangement of illumination and imaging paths resulting in a shallower depth of focus and an enhanced contrast than are otherwise achievable using non-confocal arrangements. While from some technical points of view the illumination and imaging arrangements of some embodiments of the invention may properly be regarded as "partially confocal" or "of the confocal type", the essential feature of the invention is that a shallow depth of field and an enhanced contrast are achieved based on the principles of one type of confocal microscope. Nipkow discs, if used in apparatus or method of the invention are used effectively as neutral-density filters.

The apparatus thus enables the fundus, the retina and the choroid, to be examined using a shallow depth of focus. This is an advantage as an operator can see an image of blood vessels within a relatively narrow layer of the fundus, typically within a depth of focus of about 50 µm and preferably 30 µm. As the total thickness of the fundus is several hundred microns, the apparatus enables fundal examination layer by layer. Disease associated with neovascularization that disrupts the layered structure of the fundus is more easily observed at an early stage—for example, bulges in the retinal pigment epithelium due to growth of a few new blood vessels below are more easily detectable than hitherto.

Nipkow discs comprising a plurality of apertures are used to achieve confocal arrangement of the illumination and imaging means, and are preferably mounted in operative combination with optics of the apparatus so that the planes of the respective apertures are coincidentally focused on the same layer in the fundus.

In an embodiment of the invention described below, the illumination and imaging paths each passes through a Nipkow disc adapted in use to rotate at high speeds. Preferably, the Nipkow disks are adapted to rotate at a speed of 2000–8000 rpm, more preferably at 5000–7000 rpm. Further, it has been found that good imaging is achieved in an embodiment of the invention in which rotation of the two discs is not synchronised. The two discs are thus used more as stray light attenuators or neutral-density filters to increase image contrast than as confocal Nipkow discs.

The apparatus is preferably adapted to provide a shallow depth of focus on a section of the fundus that is being viewed. It is preferred that the depth of focus be about 50 µm, more preferably about 30 µm deep, most preferably about 20 µm deep.

Fluorescein is useful for viewing neovascularization above the retinal pigment epithelium, and can be used for the viewing and diagnosis of neovascularization in diabetic retinopathy. Following administration of fluorescein, the first arrival of dye can be observed using apparatus of the invention and the operator can look to see where leakage of dye occurs, possibly indicating new blood vessels. Additionally, if tagged blood cells are used the observer may observe the movement of individual tagged blood cells in the retinal capillary network. If a tagged cell movement is irregular in its speed and course or if it stops abruptly or reverses its direction of motion, the location of such behaviour may be considered as a suspect area. The apparatus can thus be used to look at the retinal capillary network where ischemia and/or blockages have likely occurred.

For examination of glaucoma, the effects of the changed intraocular pressure can be seen using dyes and/or tagged blood cells. The apparatus offers a means to examine in details the optic nerve head (ie optic disc) as well as the retinal nerve fibre layers.

In examination of age-related macula degeneration, new blood vessel growth under the retina at the RPE level can ultimately lead to retinal damage and subsequent blindness. The disease is thought to be caused by a small number of new-growing blood vessels. By focusing on adjacent layers in the fundus (using the apparatus' shallow depth of focus), an operator can image these layers and reconstruct a 3-dimensional image of the fundus. Neovascularization intruding into the plane in focus would appear as a small area with brighter and/or clearer fluorescence signals standing out from the darkened, blurry (out of focus) and planar background (below the depth of focus of the apparatus). The apparatus of the invention, using confocal microscopy, thus enables identification of areas of new blood vessels and their growth into the plane of focus of the apparatus.

In a particular embodiment of the invention, infra-red light is used in combination with a dye that is excited by infra-red light for examination of blood vessels below the retinal pigment epithelium. Generally, visible light is not able to penetrate below the pigment epithelium and thus can not easily be used for visualisation of blood vessels in these layers. With infra-red light, which can penetrate deeper below the retinal pigment epithelium, choroidal blood vessels can be imaged with enhanced quality by using an infra-red-excited dye. A specific embodiment of the invention, described below, uses a laser source of infra-red light. A technique of the apparatus of the invention is to search the fundus in the region of the macula at low magnification, inject the infra-red fluorescent dye and focus slightly below, on or slightly above the retinal pigment epithelium. The operator then looks for a strong localised fluorescent signal slightly above the plane of the epithelium. Once an area of higher intensity signal has been obtained, the operator can use higher magnification to look at that region in more detail.

The invention also relates to ocular examination using more than one fluorescent dye. According to a second aspect of the invention there is provided ophthalmologic examination apparatus comprising:

illumination means for directing light along an illumination path and onto the fundus of an eye of a patient;

imaging means for directing fluorescence from the fundus of the patient along an imaging path to enable an image of the eye to be viewed;

a first source of visible light; and a second source of non-visible light;

wherein the apparatus further comprises selector means comprising optical elements moveable between a first position in which light from the first source is directed along the illumination path and light from the second source is directed away from the illumination path, and a second position in which light from the second source is directed along the illumination path and light from the first source is directed away from the illumination path.

The terms "visible" and "non-visible" are intended as relative terms. A source of visible light for the purposes of the invention may also be a source of a small proportion of non-visible light but is so referred due to its provision of visible-light. A source of non-visible light, likewise, may be a source of some visible light but is so referred due to its function in providing non-visible light to excite a fluorescent dye that is excited by light in the non-visible range. Whatever sources are used, appropriate filters ensure light of the desired wavelength passes along the illumination path.

An advantage of this aspect of the invention is that it enables simultaneous use of two dyes during the course of a single eye examination. One dye is excited by visible light and the second is excited by non-visible light. Different dyes can be used to look at different parts or layers of the eye or different features of the same part of the eye. Another advantage is that one light source may be used for treatment of neovascularization, or for both examination and treatment.

In an embodiment of the invention described below, the apparatus is adapted for use with a plurality of fluorescent dyes, for example a combination of dyes comprising at least one dye that is excited by light in the visible spectrum and at least one dye that is excited by light in the infra-red spectrum. In typical use, a first dye is injected and observed in the eye using, say, visible light. Subsequently a second dye is injected and observed using infra-red light. This way an operator can observe the initial appearance of each of the dyes in blood vessels. Also, dyes can be injected simultaneously and the operator can switch between light sources to observe the dyes in turn.

In another embodiment of the invention, both visible and non-visible illumination are input into the illumination path simultaneously, ie two different dye-excitation wavebands are incident on the fundus at the same time. Optical-mechanical switching between the two sources is not necessary. In this configuration, simultaneous capture of two images (one of each dye as they both appear at almost the same instant) is possible if the imaging path is split into two branches immediately after the objectives subassembly. Each branch leads to its own image intensifier-camera system (which may be especially sensitized to a particular dye fluorescence waveband). The "bifurcation" of imaging path can be achieved using a specially designed dichroic mirror or prism. Simultaneous images thus captured can be used to compare, analyze (such as by software) and confirm suspect areas of microcirculation (almost) immediately.

Preferably, the apparatus is adapted for use with a mixture of dyes in which one dye is optimally excited by light having wavelengths between 400 and 495 nm and when excited emits at a wavelength between 505 and 560 nm, and a second dye which is excited by non-visible light having a wavelength of between 770 and 780 nm and when excited emits at a wavelength of between 790 and 870 nm.

In a preferred embodiment of the invention, the second source of non-visible light comprises a laser source of non-visible light. For illumination with laser light, the laser of a specific embodiment of the invention is adjusted to provide infra-red light of about 777 nm, this wavelength being chosen so as to be suitable for use with the dye ICG dye. The filter used in combination with ICG and the laser source is thus adapted not to transmit light of wavelength 777 nm but to transmit fluorescent light of wavelengths emitted by ICG so that a usable signal, preferably a maximal signal, can be passed to the image intensifier.

In a particularly preferred embodiment of the invention the second light source comprises a laser source of infra-red light whose intensity is variable between a low power adapted for viewing the eye and a high power adapted for treatment of neovascularization.

In a specific embodiment of the invention, the treatment path is separate from the illumination path, so that the laser power is not reduced by the optics of the apparatus. Typically, treatment power anywhere between 200 mW and 2.2 W (diode output) is available, although as the apparatus of the invention enables simultaneous treatment and viewing of that part of the eye being treated, it is an option to start laser treatment at a low power and continuously observe the treatment at low power until the operator perceives that the part to be treated has been exposed to ample laser beam energy as to effect the treatment. This enables highly accurate treatment to be obtained using the apparatus.

To protect the image intensifier from the intense treatment laser pulse, a shutter (in the form of a chopping blade) is optionally installed between the objectives and the image intensifier. The shutter is driven by a rotary solenoid which, when activated by a footswitch, rotates very rapidly through 90°, bringing the blade into the imaging path in front of the intensifier. At the limit of this motion, the blade activates a limit switch which then fires the treatment laser. Specially designed delay circuitry automatically releases the solenoid after approximately 1 second, at which time, the laser pulse will have ended. The treatment laser pulse is typically restricted to last no more than 1 second.

According to a third aspect of the invention there is provided ophthalmologic apparatus for examination of an eye of a patient using two or more fluorescent dyes, comprising illumination means for directing light along an illumination path onto the fundus of an eye of the patient;

imaging means for directing fluorescence from the fundus along an imaging path for viewing an image of the fundus of a patient;

a first source of light adapted to excite a first dye;

a second source of light adapted to excite a second dye;

a first filter assembly adapted selectively to transmit light into the eye that will excite the first dye and further adapted selectively to transmit fluorescence from the first dye along the imaging path;

a second filter assembly adapted selectively to transmit light into the eye that will excite the second dye and further adapted selectively to transmit fluorescence from the second dye along the imaging path; and selector means moveable between a first position in which light from the first source is directed along the illumination and imaging paths and through the first filter assembly and a second position in which light from the second source is directed along the illumination and imaging paths and through the second filter assembly.

A "filter assembly" may be composed of 2 filters, such as 2 filter wheels, in the separate optical paths: one for excitation (in the illumination path), and, one for imaging (in the imaging path). It is further possible for a filter to transmit both excitation and fluorescence signals.

The illumination through the excitation filter wheel may remain in the illumination path; this illumination is suppressed by the second filter wheel so that excitation wavebands never enter the imaging path.

Each filter assembly is typically composed of a pair of filters—one in the illumination path that selects the excitation illumination to excite the dye and one in the imaging path to select the fluorescence waveband to view an image. A filter to select the excitation illumination is optionally omitted where illumination is by laser.

The various dye-specific excitation illumination wavebands can be provided by physically different light sources (such as lasers, lamps, LEDs). Such configurations will generally require optical switching between the sources and also, do not preclude specific filtering. Alternatively, a single lamp source (such as a tungsten-halogen bulb) which provides a broad spectrum of illumination, can be used with appropriate filters to attain the various wavebands. In the latter case, there is no need for a selector means to deflect the light into the illumination path. In another embodiment of the invention in which separate light sources are used to provide the different excitation wavebands, an opto-mechanical selector means is needed to select which light source is to direct its beam into the illumination path. In this embodiment, when the selector means is in a first position, light from the first source is transmitted along the illumination path, and when it is in a second position, light from the second source is transmitted along the illumination path. An excitation filter assembly (from which particular dye-specific filters can be chosen) may still be placed in the illumination path in order to condition the chromatic properties of the illumination (from whichever light source selected). The selected filter must be coordinated with the particular dye in use and with the light source waveband.

In use, an operator may choose the waveband of the excitation light the eye is to be illuminated with according to the layer of the fundus to be examined and the disease to be examined, depending on the dye to be used. Conveniently, the light sources and selector means are arranged so that in use the operator can switch back and forth between the sources and the excitation filters so as to match a particular filter to condition the illumination optimally to excite the specific dye being observed during the course of an eye examination.

Typically, the light from the first source differs significantly in nature from the light from the second source. In an embodiment of the invention described below, the first source generates light in the visible range and is adapted to excite the dye fluorescein, and the second source generates laser light in the infra-red range and is adapted to excite the dye ICG.

The filter assemblies are preferably according to the sixth aspect of the invention, described below.

In another embodiment, the light from the two sources of illumination may be simultaneously input into the same one illumination path so that two different wavebands (for two different simultaneously-injected dyes) illuminate the fundus. In this embodiment, simultaneous capture of the two (different dyes') fluorescence is possible using two separate intensifier-camera systems each placed behind appropriate barrier filters. The different fluorescence can be separated using an appropriate dichroic mirror or prism.

In another embodiment of this aspect of the invention, the apparatus further comprises a laser source of infra-red light for treatment of neovascularization by cauterization or photocoagulation.

A fourth aspect of the invention provides a method of diagnosis of disease in an eye of a patient, comprising:
  providing in the ocular circulation of the patient:
    a first dye which fluoresces in response to illumination at a first predetermined wavelength; and
    a second dye which fluoresces in response to illumination at a second predetermined wavelength;
    wherein the first and second dyes fluoresce at different wavelengths;
  illuminating the fundus so as to excite the first dye at the first predetermined wavelength, and viewing an image of the fundus by viewing the fluorescence from the first dye; and
  subsequently illuminating the fundus of the patient so as to excite the second dye at the second predetermined wavelength, and viewing an image of the fundus by viewing the fluorescence from the second dye.

Preferably, the method comprises the use of barrier filters to block out undesired reflection or scattering of the excitation illumination (and pseudo- and auto-fluorescence) from entering the imaging path. For example, when viewing the fluorescence from the first dye, a filter is used preferentially to transmit substantially all fluorescence from the first dye only.

The invention also provides, in a fifth aspect, a method of examining the fundus of a patient by:
  focusing on a thin layer of the fundus;
  focusing on an adjacent thin layer of the fundus; and
  constructing a 3-dimensional image from the imaged layers of the fundus.

The imaged layers are typically of around 30 $\mu$m deep, preferably less than 20 $\mu$m deep. Focusing can occur in steps of overlapping layers, storing the images of all the overlapping layers viewed so that a final 3-dimensional image can be constructed from the stored layer images by aligning the latter images.

The invention also provides, in a sixth aspect, 3 pairs of excitation and barrier filters in 2 separate filter assemblies for use in fluorescence microscopy comprising:
  (1) a first filter for fluorescein adapted to transmit substantially all light of wavelength between 410 and 475 nm and to block substantially transmission of all light of wavelength above 510 nm; and
    a second filter for fluorescein adapted to block substantially transmission of all light of wavelength below 500 nm and to transmit substantially all light of wavelength above 540 nm;
  (2) a first filter for PKH26 adapted to transmit substantially all light or wavelength between 450–550 nm and to block substantially transmission of all light of wavelength above 590 nm; and
    a second filter for PKH26 adapted to block substantially transmission of all light of wavelength below 560 nm and to transmit substantially all light of wavelength above 605 nm; and
  (3) a filter for ICG adapted to transmit substantially all light or wavelength longer than 810 nm and to block substantially transmission of all light of wavelength shorter than 790 nm.

The invention thus provides a system which can view to the level of tens of microns and can differentiate the layers in the fundus—to be able to discern, for example, a vessel growing out of the plane of the capillary network. Lastly, it can be adapted to view below the opaque retinal pigment epithelium by imaging in the (near) infra-red waveband using indocyanine green (ICG) dye. The layering or sectioning is achieved using confocal microscopy to attain the required shallow depth of focus. When the focal plane of the apparatus is positioned slightly above the capillary net or the retinal pigment epithelium (ie the latter plane is slightly beyond and below the apparatus focal plane) a vessel growing out of the plane of the capillary net will come into focus and thus is observable as an area of strong, in-focus dye fluorescence against a blurred background. The contrast is enhanced using a combination of the Nipkow disc and a suitable filter to transmit ICG fluorescence.

Immediately after injecting the dye, the invention enables observation of the advent of the dye in the fundus, using a high-speed imaging system. In this embodiment, the apparatus remains focused at a suspect area. When the dye first appears in the fundus, a fluorescence signal from any neovascularization in the focal plane of the apparatus, is expected to be observed more clearly and more strongly than the rest of the capillary net (which is outside of and below the focal plane of the apparatus, and therefore is in the blurred background).

A different method can also be used to locate neovascularization, and/or corroborate the findings of the above-described technique. This is achieved by following the movement of tagged or marked blood cells. Red blood cells are withdrawn and prepared by attaching a special dye-marker such as PKH26—which is currently not approved for human use—to each cell. The cells are then re-injected into the blood stream. By observing the movement of the tagged cells, it may be possible to observe blockages in vessels. It may be also possible to correlate blood cell motion to the effects of increased intraocular pressure (glaucoma) on the blood flow, and the effects and efficacy of drugs and their therapies. It may be also possible to observe capillary blood flow in the optic nerve head (ie optic disc). Other statistics which may also be deduced from the movement of the cells are blood velocity and blood volume. Regardless of which embodiment of the invention, illumination can be focused into a small spot on the fundus. This aspect of the apparatus can be used to direct wavelength-specific illumination to activate specially tailored drugs in Photodynamic Therapy.

BRIEF DESCRIPTION OF THE FIGURES

The invention is now described with reference to drawings illustrating a specific embodiment of the invention in which.

DETAILED DESCRIPTION OF THE INVENTION

Figure 1:
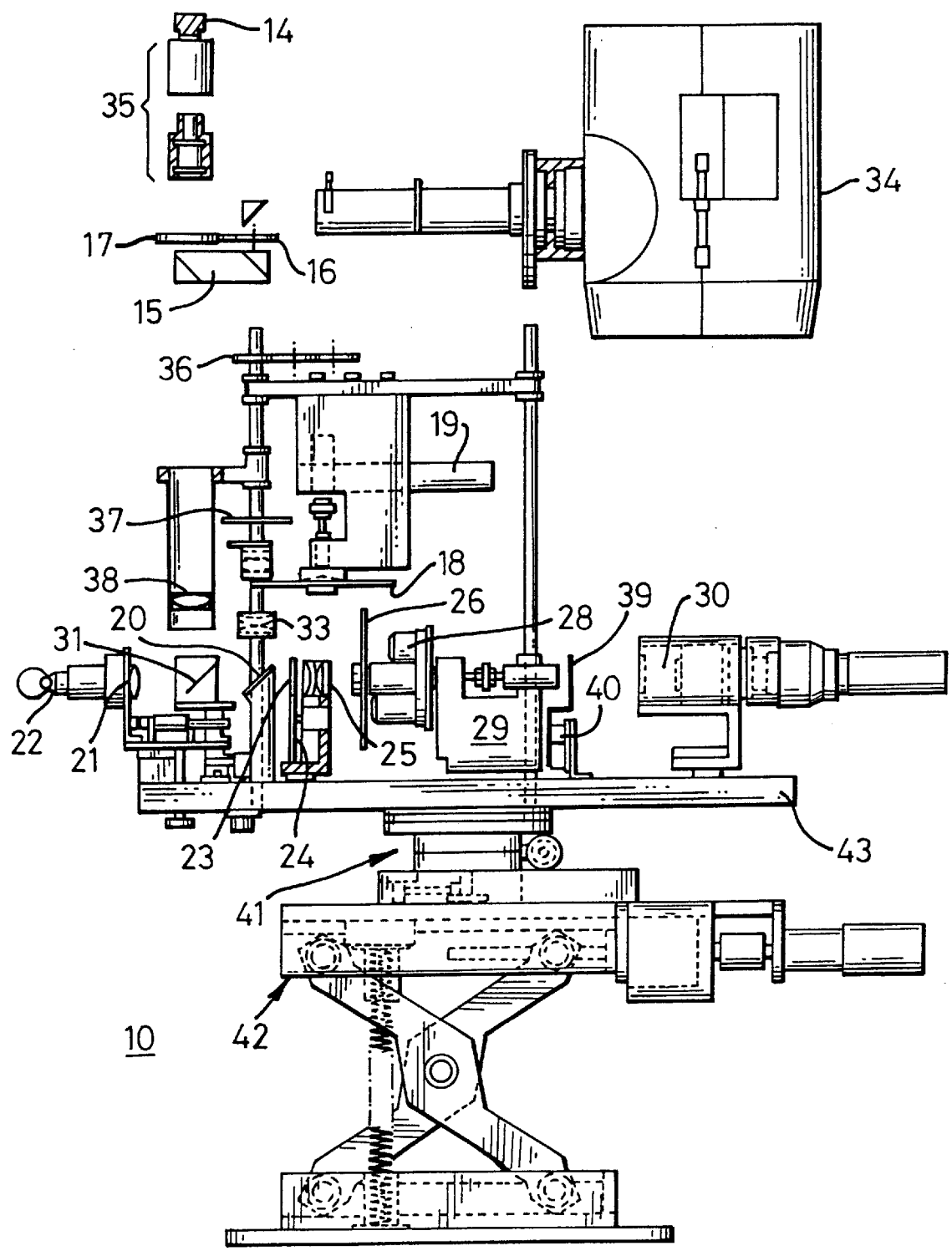
FIG. 1 shows a schematic side view of apparatus according to the invention.
Figure 2:
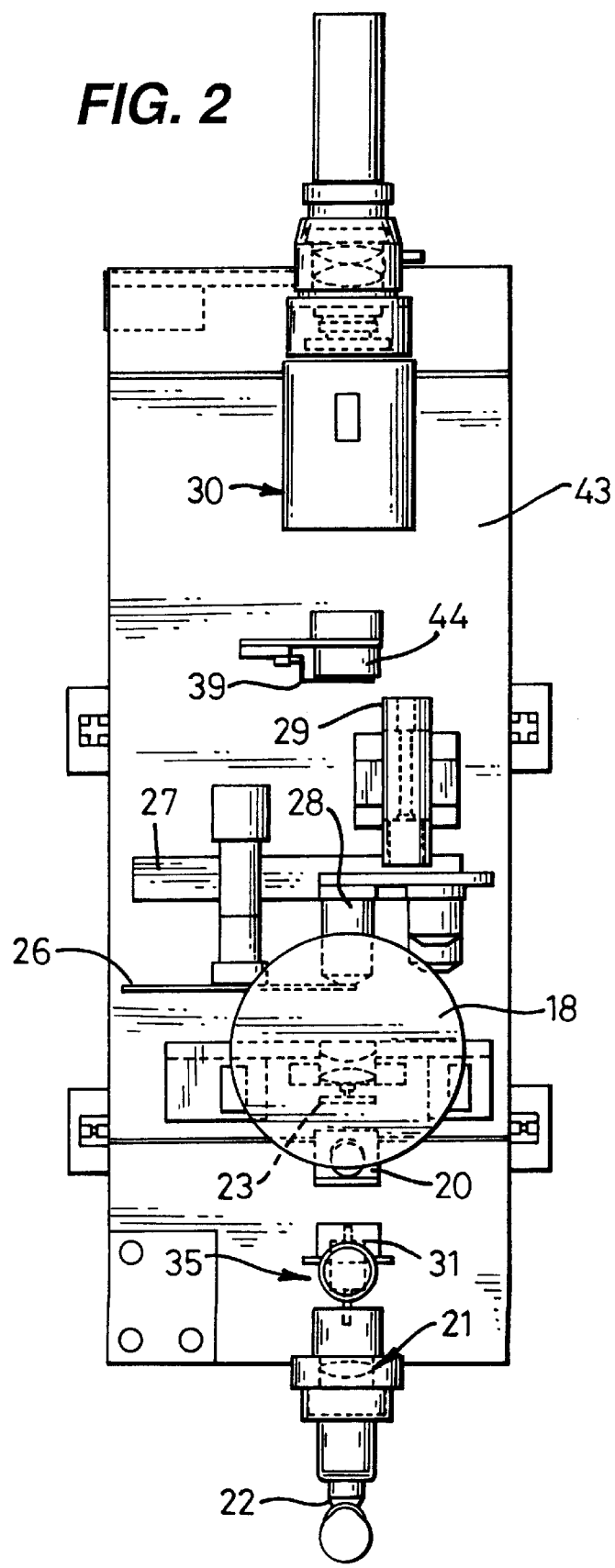
FIG. 2 shows a schematic plan view of the apparatus.
Figure 3:
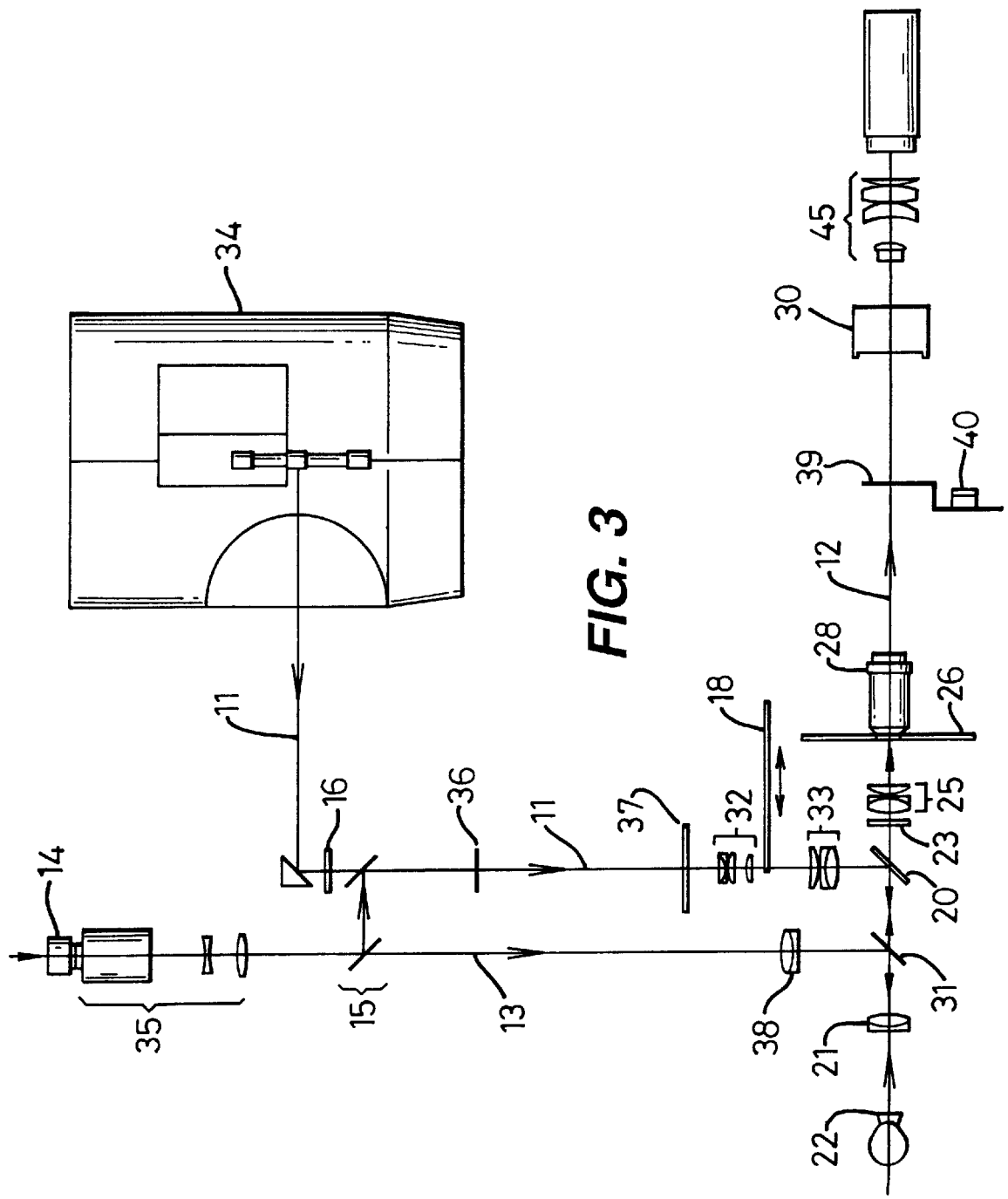
FIG. 3 shows a schematic side view of the optical layout of the apparatus.

Referring to FIGS. 1–3, the apparatus according to the invention is shown generally as 10. The apparatus comprises three optical paths which converge and coincide just before the eye. The optical elements inserted in each path are varied according to design. The three paths are:

i. the illumination path (11), ii. the imaging path (12), and, iii. the treatment path (13).

The components, their housings and holders of the imaging path are set and aligned on a 20 mm-thick, steel base plate. The components of the illumination path are aligned and supported by the front two (of four) steel, threaded rods screwed vertically into the base plate; while the illumination sources are supported above the base plate by four square cross-section, aluminium rods (screwed onto the side of the base plate). The components of the laser treatment path are also supported by the 2 front threaded rods.

The apparatus itself is supported by the following assemblies and systems:

i. coarse translation stage;

ii. electronic control unit;

iii. imaging hardware (intensifier, CCD camera, frame-grabber and computer) and software.

A television monitor with videotaping capability may be added for making continuous, low-resolution recording.

I. The illumination path comprises the following components (in order of location along the direction of travel of the illumination beams):

a. 2 sources—a mercury arc lamp and a diode laser (14); or, a tungsten-halogen lamp;

b. optical switching assembly (15) for switching between the two sources (not required with the tungsten-halogen source);

c. excitation filters (varied according to sources used) (16) on a filter wheel (17);

d. illumination lens group #1 (32);

e. illumination Nipkow disc (18) and motor assembly (19);

f. illumination lens group #2 (33);

g. cored mirror (20);

h. focusing lens group (21) and contact lens (22).

II. The imaging path comprises the following components (in order of location along the direction of travel of the fluorescence signal):

a. contact lens (22) and focusing lens group (21);

b. imaging filters (varied according to sources used) (23) on a filter wheel (24);

c. imaging lens group (25);

d. imaging Nipkow disc (26) and motor assembly (27);

e. microscope objectives (28) and motor assembly (29);

f. image intensifier (30) with coupling relay lenses and CCD camera.

The signals from the camera goes to a 486DX4 computer. The computer holds the frame-grabber (DIPIX XPG-1000 Power Grabber).

THE ILLUMINATION PATH

1. Illumination

To maximize the input light intensity, the sources are mounted on the top of the apparatus (10). In this way, no light is lost through coupling with fibre optic light guides or (the mechanical problems associated with) fixtures such as mirrors on an articulated arm. The IR laser (14) runs at about 780±5 nm and is used to excite ICG. The narrowness of the radiation reduces chromatic aberration problems and produces high-contrast, sharp images. By increasing the power, the same laser may be used for photocoagulation, ie treatment. The diode (SDL-2372-P1) is made by Spectral Diode Laboratory in the US and is driven by an SDL-820 Driver. Both visible and laser beams are collimated at the sources, ie before either beam enters the illumination path. The visible (mercury) source is pointed forwards, parallel with and above the axis of the imaging path. The laser beam is pointed downwards along the treatment path.

The mercury lamp is used to provide general viewing illumination, and for fluorescein excitation in 460–490 nm and PKH26 excitation in 530–560 nm. It is strong enough to provide other wavebands (using the appropriate filters) for other dyes.

To reduce cost and obtain better intensity control, a tungsten halogen lamp (with a dimmer controller) or any broad-band source may be used instead. This single-lamp source configuration can replace both the laser diode and the mercury lamp as it outputs broadband radiation of 400 to 800 nm. In such a configuration, there is no laser to provide both NIR low-power illumination and high-power treatment. The single lamp with appropriate filtering provides all the continuous and simultaneous low-power illumination required for viewing. A separate high-power laser output can be inserted into the treatment path via a fibre-optic light guide. The choice of the laser line (ie treatment wavelength) will depend on factors such as the area to be treated (ie pigmentation), the dyes used, etc. Such a treatment source (usually) includes an aiming beam for pointing the treatment spot. The main issue in the choice of the light is beam-conditioning and waveband reduction to minimize chromatic aberration. It should be noted that at the time of fabrication of the various embodiments of this invention, there is currently no internationally (or even nationally) accepted standards or guidelines on the safety limits of illumination on the human eye from any broadband (extended) sources including the tungsten-halogen and the mercury arc lamps.

The collimated beams are passed through a series of black, PVC tubes (not shown) as they proceed along the illumination path (11) to minimize scattering or reflected light from entering the imaging system.

2. Optical Switching Assembly (15)

The outputs of the illumination sources fall on a set of three, 45°, right-angle prisms. One prism, with a broad-band coating maximally deflects the visible light from the mercury lamp vertically down the axis of the illumination path. The collimated laser output, when used for illumination, is deflected by two specially coated prisms (in a periscope-like arrangement) into the same illumination path.

The three prisms are fixed on a bar which is mounted on a bearing slide. A geared rack is also attached to the bar. A pinion gear driven by a stepper motor contacts the rack. Controlled by the computer, the prism assembly can be moved into two positions:

Position #1: excludes laser light from and deflects visible light into and along the illumination path;

Position #2: excludes visible light from and deflects laser light into and along the illumination path.

The accuracy of these two positions is measured by the count of the stepper (ie linear motion converted to the number of step count which is transposed into linear motion) from a reference Hall-Effect sensor position. At start-up or reset, the stepper turns until the sensor find a magnet (on the prism bar) positioned such that the visible light is deflected into the illumination path (ie Position #1). If the laser is to be used for illumination, the stepper rotates a pre-calculated, calibrated number of steps to bring the (periscopic) prism set into Position #2 to deflect the collimated laser beam into the illumination path. When the laser beam is used for illumination, the visible beam is deflected away from the illumination path, ie it is excluded, and, vice versa.

In an embodiment to provide continuous and simultaneous illumination in the two-source configuration, the optical switch is removed. The two specially coated prisms (in a periscopic arrangement) are changed to two dichroic mirrors and repositioned (from above to) below the filter wheel (17). The first mirror the laser beam encounters is coated to maximally deflect the 780 nm beam through 90°. The second mirror is positioned below the filter (16) to maximally deflect the laser beam through 90° downwards into the illumination path. This latter mirror will also transmit visible illumination (400–700 nm) from the mercury source. These mirrors are thus fixed in those positions, and, VIS and NIR radiation can enter the illumination path simultaneously.

3. Excitation Filters (16) and Filter Wheel (17)

The aluminium filter wheel (17) is a circular plate with five equally, angularly spaced filter "slots". Only four slots are used; two of which are excitor filters. They are:

a. Fluorescein excitor filter transmitting maximally (80% average) between 400 and 490 nm;

b. PKH26 excitor filter transmitting maximally (70% average) between 400 and 550 nm; this filter is currently stacked with a fluorescein barrier filter (see below) to produce a narrower green bandwidth for better viewing (by reducing chromatic aberration);

c. empty slot for the laser beam (ie for ICG excitation which does not require an excitor filter as the laser bandwidth is narrow);

d. neutral-density filter stack to reduce the intensity for general viewing; and, e. hot mirror filter which transmits 400–650 nm and reflects wavelengths longer than approximately 700 nm ie near IR; this filter is currently stacked with a PKH26 barrier (see below) to produce a narrower violet bandwidth for better viewing (by reducing chromatic aberration).

The thin-film coatings of these circular filters are designed and fabricated in-house, are especially durable, heat-resistant, and have especially steep or sharp edges at specifically prescribed wavelengths. The required reflection-transmission characteristics are applied to one side; while the appropriately matched anti-reflection multi-layer coatings are applied to the other face to reduce reflection losses.

The glass (BK7) is also polished in-house. The visible excitation (and barrier) filters are "powered" in that they are flat on one side and slightly concave on the other surface. The large radius of curvature (R>1200 mm) is introduced to compensate for the unavoidable optical aberrations in having to view across the entire visible and the near IR spectra. ICG filters are fabricated from plano-plano (BK7) windows.

Any of these five filter positions can be selected via the computer (control). The movement is driven by a stepper motor and the accuracy of the positioning of the selected filter with respect to the illumination path is by one Hall-Effect sensor which senses a reference (start-up or initialization) position. The algorithm is such:

i. at start-up or reset, the wheel rotates until the sensor picks up the position of a magnet on the wheel; this is the reference position;

ii. when a filter is selected, the stepper counts the required number of steps (transposed from the degrees of rotation) from this reference position, ie multiples of 72°;

iii. at every request to position a different filter, the stepper rotates to find the reference position before counting to the correct position for the required filter.

These hardware and software algorithms may be extended in the future. Different filters to suit the wavebands required may, of course, be installed.

Whether one- or two-source, two optical elements to alter the illumination are deployed. These are a. light-shape diffusers (LSDs); and, b. a circular linear-wedge neutral-density filter.

These elements modify the beam shape and augment illumination intensity control, respectively. The LSDs are placed on a filter wheel (similar to (17, 24)). The LSDs "scatter" the collimated (VIS and/or NIR) beam into ½°, 1°, 5° and 10° angles, thereby increasing the area illuminated as well as reducing the intensity over the area. The intensity can be further attenuated by rotating the circular linear-wedge neutral-density filter which has a continuous, smoothly increasing broadband attenuation characteristic around the circular plate. This filter is placed immediately below the selected LSD.

4. Illumination Lens Group #1 (32)

This group of lenses is made up of a doublet and two singlets, made and coated in-house. It focuses the incoming collimated beam (visible or laser) onto the Nipkow disc (18) pattern plane ie the plane of the disc pattern is coincident with the back focal plane of this lens group. The lens coating is for broadband anti-reflection. The group is held in a housing which is suspended along the two front threaded rods, above the Nipkow disc.

5. Illumination Nipkow Disc (18)

This disc is horizontal with the illumination beam at normal incidence. The pattern comprises slits or pinholes in 3 mm-wide tracks. The pattern is etched on a thin aluminium coating deposited on one side of a 2 mm-thick BK7 glass disc of Φ100 mm. The track pattern lies in the coincident focal planes of the lens groups above and below the disc. The track pattern (currently in use) is ordered such:

Track #1 R50–47 mm—clear glass, no pattern;
Track #2 R47–44 mm—50 μm slits arranged along Archimedes spirals;
Track #3 R44–41 mm—40 μm slits arranged along Archimedes spirals;
Track #4 R41–38 mm—30 μm slits arranged along Archimedes spirals;
Track #5 R38–35 mm—20 μm slits arranged along Archimedes spirals;
Track #6 R35–32 mm—50 μm pinholes arranged in a square lattice;
Track #7 R32–29 mm—40 μm pinholes arranged in a square lattice;
Track #8 R29–26 mm—30 μm pinholes arranged in a square lattice;
Track #9 R26–23 mm—20 μm pinholes arranged in a square lattice;
Track #10 R23–21 mm—10 μm pinholes arranged in a square lattice.

The area with R<20 mm is inaccessible due to mechanical obstruction. The number of arms of Archimedes spirals and the square lattice spacing are determined by the estimated transmission of light through the pattern as it spins. The range of the transmission is between 3 and 7%. The pattern on the Nipkow discs has fixed throughput. As neutral-density filters, they are therefore restricted to these percentages of transmission. Hence, the presence of the circular linear-wedge neutral-density filter described earlier to enhance intensity control, if needed.

The disc is spun on a shaft which is coupled directly to a dc motor (19) held in the same housing. The speeds of rotation range from 1000 to 800 rpm. Speed adjustments and changes are controlled by the electronic control unit which receives commands from the computer. The edge of the disc (at R50 mm) must not vary by more than 400 μm from exact perpendicularity to the rotating shaft.

The housing holding the disc, the shaft and the motor sits on a motorized slide which moves the plane of the disc in a horizontal direction through the illumination beam ie changing tracks. The slide receives a signal from the computer (through the electronic control unit) to move to the various track positions. The slide is held on a block which is suspended by the four threaded rods. At initialization, the slide moves the disc and its housing assembly until the latter hits a limit switch which is a limiting reference position. From there, the disc is moved to the centre (R48.5 mm) of the first (clear glass) track. The disc is considered initialized and awaits the user's commands to move to any other track by moving in 3 mm steps.

The Nipkow discs prevent or restrict stray or scattered light from entering the respective paths. The signal-to-noise ratio is increased. The depth-of-focus is small. In the case of illumination, the disc can be thought of as lighting a thin layer about the focal plane of the apparatus. The imaging disc discriminates all signals, passing only those fluorescence signals from that illuminated layer.

In another embodiment of the Nipkow discs subsystem, the two discs (in their separate paths can be aligned and driven by one motor. In such a configuration, the shafts of the two discs are aligned parallel to one another in their separate holders. The two shafts are coupled together using a no-slip belt of suitable length and pre-tension such that it moves without obstructing the beam paths. The motor is mounted on one housing (preferably that of the illumination disc) to drive both discs simultaneously and in an aligned and synchronized manner.

6. Illumination Lens Group #2 (33)

This group is made up of a singlet and a doublet which are different from those in group #1 (32). These lenses are also made and coated in-house. They collimate the diverging rays from the Nipkow disc (18) ie the disc pattern plane is the group's front focal plane. The coating is also broadband anti-reflection. The group is held in a housing which is suspended along the two front threaded rods (below the Nipkow discs).

7. Cored Mirror (20)

The re-collimated beam (from illumination lens group #2) falls on a 45° mirror (20) with a hole in its centre. The mirror is such that when observed from the top, ie in the direction of illumination, it appears to be a square mirror with a round hole. Light passing through the hole is not allowed to reflect back out into any optical path. (The surfaces below the hole are blackened.) Light that falls on the mirror surface around the hole is deflected into a horizontal, collimated (annular) beam, directed forward, towards the eye. The mirror and its holder are fixed to the base plate after initial alignment.

8. Focusing Lens Group (21) and Contact Lens (22)

The horizontal, collimated illumination falls next on a doublet (21). The distance between the cored mirror and this doublet is about 70 mm. This gap is required for the insertion of the laser mirror (31). The doublet is identical with the one in Illumination Lens Group #2 (33), ie the same glass, size, coating, etc. The doublet holder is bolted to a motorized slide. The slide is similar to that for the Nipkow disc except that it is "folded" such that the driving motor lies beneath the slide table. The user may move the doublet forward or backward (ie change the position of the back focal plane of the doublet) directly by using push buttons (on the X-Y-Z translation stage control panel) or by using the computer to move it in steps of either ~½ mm (coarse) or ~15 μm (fine). (This latter control is to be used in certain image capture processes.) The slide allows a total doublet displacement of ±10 mm which is approximately equivalent to a variation of ±10 dioptres in the power of the eye being examined. The slide is fixed to a small plate which sits on a ball-bearing slide table. The slide table is bolted to the front edge of the base plate.

A contact lens (22) sits in a conical holder-housing and is also fixed to the same small plate (on which sits the motorized slide moving the focusing doublet, ie the doublet can be moved with respect to the contact lens). The lens is ~60 mm in front of the focusing doublet in its nominal position. This contact lens is designed, fabricated and coated in-house. The light from the doublet passes through this contact lens into the segments of the eye in contact with the forward surface of the contact lens. The conical holder provides the separation or clearance needed (about 50 mm) between the front edge of the base plate and the nose of the animal or human. The contact lens provides a fixed surface or window through which light can pass into and out of the ocular media.

Hence, the contact lens and the focusing doublet both "float" on the ball-bearing slide table; while the doublet can move (with respect to the contact lens) to change the apparatus' focusing plane. The ball-bearing slide table minimizes the force the instrument applies to the cornea and the ocular media. (The specification is for an applied force of less than 15 gf.) Hence the contact lens will very gently touch the cornea and be held in contact by the surface tensional forces exerted by the methyl-cellulose, (a viscous fluid used to provide an intermediate, filling medium to reduce the refractive index difference between the contact lens and the cornea), aided by a pre-load (of <15 gf).

THE IMAGING PATH (12)

1. Contact Lens (22) and Focusing Lens Group (21)

The imaging path (12) begins where the illumination path (outside of the eye) ends: at the same contact lens (22). The next element in the imaging path is the focusing lens doublet (21). However, the fluorescence signal passes through the hole in the cored mirror (20), continuing its horizontal traverse, parallel to the base plate, towards the rear of the instrument. Hence, the imaging (12) and illumination paths (11) share a common optical axis between the cored mirror and the eye. The cored mirror is where the two paths split at right angles from one another.

2. Imaging Filters (23) and Filter Wheel (24)

Behind the cored mirror is a filter wheel (24) which is physically the same as the illumination excitation filter wheel. This imaging or barrier filter wheel is also driven by a similar stepper motor. The five filters in use are:

a. Fluorescein barrier transmitting maximally (95% average) above 530 nm;

b. PKH26 barrier transmitting maximally (92% average) above 595 nm;

c. "hot mirror" filter which transmits 400–650 nm and reflects >~700 nm ie it blocks out IR;

d. ICG barrier transmitting <3% at 790 nm, with a rising edge of ~50% at 799 nm, and which has >70% average transmission at 810 nm;

e. ICG barrier with <10% average transmission at 790 nm, and >90% transmission at 810 nm.

There is no empty slot in the barrier filter wheel. The selection and positioning are activated and measured by the same methods as for the excitation filter wheel (17). The difference between the illumination and imaging wheels (besides the filters they hold) is that the excitation wheel is horizontal, while the barrier wheel is vertical (with its holder aligned and bolted to the base plate).

3. Imaging Lens Group (25)

This group of lenses is made up of the same doublet and singlet combination as illumination lens group #2 (33). The differences are that the imaging group is vertical and the lenses are arranged in reverse order of placement along the optical axis; the lens group housing is bolted to the base plate. The group focuses the collimated fluorescence signals onto the following imaging Nipkow disc (26). That is, the Nipkow disc pattern lies on the back focal plane of the imaging lens group.

4. Imaging Nipkow Disc (26) and Motor Assembly (27)

This entire subassembly—disc pattern, holder, dc motor, positioning motorized slide and the control thereof—is the same as the one in the illumination train. The differences are that the motorized slide is directly bolted to the base plate and that the imaging disc is vertical. By the same principle, stray or scattered light from around the layer of interest cannot pass through the spatial filtering of the small slits or pinholes. In the imaging case, the disc can be thought of as discriminating or selectively transmitting the fluorescence from a thin layer about the focal plane of the focusing doublet and contact lens, rejecting the signals from elsewhere. Note the two-disc-one-drive (synchronized) subsystem envisaged above.

5. Microscope Objectives (28) and Motor Assembly (29)

Three microscope objectives are placed behind the imaging Nipkow disc (26). These are finite objectives of 160 mm tube length. The available magnifications are:

a. 6.3X, made by Melles-Griot;

b. 10X, made by Spindler-Hoyer; and, c. 20X, made by Spindler-Hoyer.

These objectives are equally, angularly spaced on a wheel driven by a stepper motor. Each objective is positioned such that it is exactly at the "working distance" from the Nipkow disc pattern, ie each objective is focused on the Nipkow disc pattern. The positioning of each objective is sensed by a Hall-Effect magnetic sensor attached to the objectives housing (ie there are three magnets and one sensor chip; each magnet is positioned on the wheel such that when it is detected by the sensor, the optical axis of the objective associated with this magnet is collinear with the optical axis of the imaging path). By selecting "Magnify" from the monitor control panel on the computer screen, the computer sends a command to the electronic control unit which activates the stepper which rotates the objectives wheel to position the objective selected. Each click turns the objectives wheel sequentially, ie the wheel turns 120° in the same direction of rotation, to the next objective on the wheel. This simple control algorithm will be replaced by a smarter, "learning" subassembly. The holder of the objective wheel, the shaft and the stepper motor sit on ball-bearing, microslide tables which are bolted to the base plate. The microslide tables allow small positional adjustments of the objectives housing parallel with the optical axis of the imaging path. After initial calibrations and alignment of each objective's working distance (from the imaging Nipkow disc pattern), the housing is secured onto the base plate by locking screws.

6. Image Intensifier (30) and CCD Camera

The use of an image intensifier is unique to this instrument. Its presence is necessary because of the very low intensities expected from ICG fluorescence. It also allows for lower illumination intensities and/or lower dosages of dye since the intensifier can amplify weak fluorescence signals. The tube used is a standard Generation II tube (XX1440CS) with minimum 38 line-pair per mm resolution, an S20 photocathode and a P20 phosphor output. The spectral response of the photocathode extends from 400 nm to around 900 nm into the NIR. The tube axis is collinear with the optical axis of the imaging path. It sits in a housing which is held on a ball bearing, micro-slide table. The position of the tube (along the optical axis) is thus adjustable about the 160 mm tube length position of each objective. Once calibrated and aligned, its position (on the base plate) is fixed by locking screws.

The CCD camera currently in use is a PULNiX TM-6701AN. It is a high-speed (60 full frames.s$^{-1}$), progressive scan, black-and-white camera. This fast rate is required to capture the first entry and progression of the dye into the fundus with as many details as possible. The camera is coupled to the tube by a relay lens group (which is designed and built in-house).

THE TREATMENT PATH (13)

Using the laser (14) for treatment means maximizing the amount of laser power delivered to the cornea (and the fundus). However, if the treatment beam travels the illumination path (ie through all the above-described components, especially the Nipkow disc), the loss of laser intensity at the contact lens is higher than 60%. Also, as the radiation is focused onto the Nipkow disc, the concentration of energy can damage the disc coating, ie the pattern. To avoid these problems, the treatment path (13) is separated from the illumination path (11). This is achieved by the optical switch (15) outlined before. Note that this switch allows visible light to pass along the illumination path while the treatment is being carried out, (ie it is possible to view treatment in real time using visible light via the dichroic mirror outlined below).

The separation of paths is carried out by allowing the laser radiation to pass straight down from its output (and collimating elements—within the laser holder) into the 70 mm gap between the cored mirror (20) and the focusing lens doublet (21). In its simplest configuration, the treatment path contains one optical element, a BK7 mirror (31) (with a special dichroic coating). This mirror is inserted into the gap just before the treatment laser is fired. The mirror (31) sits on a platform which is held on a ball-bearing slide table. The movement and the positioning of the slide are managed by a geared rack (attached to the platform) and a pinion rotated by a stepper motor. The mirror is thus moved into and out of the gap where the laser path intersects the illumination and imaging paths. Note that this insertion and removal must also be considered in the context of laser-eye safety at the high treatment energies. The exact sequence—speeds of movement—will depend on the protocol designed or requested by the user.

The laser mirror may also be reshaped so that it can remain fixed in the treatment and illumination/imaging paths. Its shape is changed such that at 45° to the beams, its apparent shape and size fills the hole in the cored mirror. Its coating is dichroic (specially designed and fabricated in-house) for maximum reflection (~90%) of the 780 nm treatment laser at 45° incidence and maximum transmission (at >80%) of wavelengths <650 nm and >810 nm for 45° incidence. With such a design, laser light, incident along the treatment path, is reflected onto the focusing doublet and contact lens, then into the eye. At the same time, the fundus can be illuminated in the visible and/or the NIR waveband, allowing simultaneous viewing. Fluorescence signals are maximally transmitted through the laser mirror (31), along the imaging path to the intensifier. The treatment laser line is rejected. The laser mirror (31) thus need not be moved, as movement incur safety considerations in reproducibility, etc.

The laser output power adjustments, whether for illumination or for treatment, are controlled by the diode driver (SDL-820). The diode can output a maximum of 2.2 W in continuous, pulse or single-pulse modes. Regardless of the treatment laser chosen, all intensity or power adjustments are made on the driver's control panel itself. For safety reasons, output level controls are not integrated into the prototype. However, a safety "remote interlock" to turn off the driver in an emergency is available.

The high-power laser inserted into the treatment path (in the 1-illumination source configuration) is a Laserex LP-1800 providing up to 2 W at 810 nm. It is delivered through a choice of a $\Phi 100$ $\mu$m or $\Phi 200$ $\mu$m fibre optic light guide which also incorporates a low-power (<1 mW) red (~633 nm) aiming beam at its output. An exact copy of the focusing doublet (21) is inserted into the treatment path to collimate the output of the fibre optic light guide. Laser power and duration are pre-set on the laser driver panel. The laser is fired by the activation of a limit switch positioned at the end of the motion of a chopping blade. The blade is rotated into the imaging path in front of the image intensifier tube by a rotary solenoid (which is activated by a footswitch). Upon execution of the firing sequence, the blade remains in the imaging path for up to 1 second.

THE COARSE TRANSLATION STAGE

Forward-backward (X) and left-right (Y) coarse translations are provided by two Newport low-profile translation stages (426 Series), each driven by a Newport 860A-2 motor. These are dc, continuous drives (although the minimum increment is specified at 0–5 $\mu$m). The up-down (Z) motion is driven by a dc motor coupled to a Newport EL-120 laboratory jack. The Newport X-Y stages sit on top of the jack. There are no sensors to set reference positions. However, two limit switches are installed for each direction to cut off the current to the motor of the stage which has reached an extreme position. The load on the Z stage is reduced by two sets of compression springs installed on either side of the jack. This compensation allows for faster Z motion without straining the electrical output of the power supply to the motor. These stages are not computer-controlled. They move independently under the control of the separate hardware control panel. The motion of each stage (X,Y,Z) is directed by 2 buttons and a speed control knob on the panel. The entire X-Y-Z assembly can be detached from the base plate.

THE ELECTRONIC CONTROL UNIT (not shown)

The electronics controlling the motors (and movements of the optical components) are designed and fabricated in-house. The central or "master" controller is based on the Intel 8051 series of micro-controllers. This chip is programmed with a set of instructions. Each instruction is recalled and activated when the chip receives the proper codes from the computer. The instruction set was written in-house.

Besides the main PCB holding the micro-controller, there are six other PCBs. Each PCB controls up to two stepper or dc motors. The micro-controller co-ordinates the sequences the various motors must move upon receiving the proper command codes from the computer. To increase efficiency, the design can be changed from the one micro-controller looking after the running of the entire electromechanical system, to several micro-controllers, each looking after not more than two motors. A master controller (ie the computer itself) will then tend to co-ordination and communication only.

THE IMAGING HARDWARE and SOFTWARE

The electronic imaging hardware or system comprises the image intensifier tube, the CCD camera and the frame-grabber (described above). There are three levels of software:

(1) Assembly language programming to control the various ICs, micro-controllers and other electronic components.

The movement of every optical element in the prototype is preprogrammed (using assembly language) into the Intel® 8051 family of micro-controllers. The same principle of operation is applied to all electromechanical components: to move to a new position (commanded by and from the computer), a. move the component (eg filter wheel (17, 24)) to its reference position (given by the position of a magnet with respect to a Hall-effect sensor; then, b. move the component to the requested position (by rotating the stepper motor by the number of pre-programmed step-counts needed).

(2) Higher level language (C++, Visual C++, Visual BASIC) programming of the (MicroSoft) Windows®-based interactive user-interface.

The user-interface is Windows®-based. The software begins with an entry or introductory screen displaying the logo and the name (of the apparatus). There are 3"buttons" (CAPTURE, HELP and EXIT) to click on (with a mouse/pointer) to select the next screen. The HELP facility includes explanations of and how to use every succeeding screen and dialogue box. All HELP pages are interconnected in that any page can be called up (for display) from any other cross-referenced page. EXIT ends the programme execution.

On selecting CAPTURE, the patient data dialogue box is shown. The user selects from a list of already-registered patients (ie in the case of a patient making a subsequent visit/scan), or enters another dialogue box to register new patients. The software automatically logs the date of the visits, the time of each scan as well as the type of each scan. Once the name of the patient is found or entered, a 4-letter "nickname" is attached for the purpose of auto-filenaming. All patients' data are stored in a master file and in the file summaries of each patients' image files. All image files are accorded the nickname as a "prefix" to the filename. The user may either elect to call up stored images (from previous visits) or go on to capture new images.

The next screen is the image display screen. If previously stored images are called, they are loaded into and displayed in this window. All image-handling utilities are available except the commands to capture new images (when there are pre-loaded images). If new images are to be captured, the user proceeds to the appropriate measurement protocol, ie triggering for dye influx, sectioning or cell-tracking. After the new images have been captured into the temporary memory, they are displayed on the screen in reduced size, usually 5-by-4 frames per screen. The user may scroll row-by-row backwards or forwards along the entire sequence captured, or, show the sequence page-by-page. The user may select particular (sequences of) captured or loaded frame(s) to:

a. store on permanent storage media;
b. magnify for closer study;
c. overlay on a "live" image;
d. show the sum with and difference from another captured image.

The last two utilities are to give the user the means to compare differences between:

a. a captured image with the live feed from the camera (on the computer monitor), and,
b. two captured images, respectively.

The trained eye will be able to notice differences in the images as the dye progressively stains the vessel walls and/or spreads or dilutes in the (micro-)circulation.

If a particular frame is magnified in the next screen, the user may, at any position within the enlarged frame, a. define a region of interest (RoI) outlined by a user-moveable box;
b. view the histogram of the RoI;
c. adjust a Look-Up Table on the RoI;
d. view a line profile (defined independently from the RoI);
e. "mark" out certain features of interest;
f. view and/or store the selected or marked feature in a special markings image file.

The latter two utilities are suitable for frames containing tagged cells The user may pick a sequence of frames showing the movement of tagged cells (within a field of view). To follow the movement of (and make subsequent calculations on) a particular cell, the user may zoom in on each frame in the sequence, mark out that particular moving cell in each frame. Once marked, the cell is surrounded by a small box; only the box and its contents are saved into an intermediate markings file. When every frame in the sequence has been studied and the cell being tracked has been marked out from each frame, the user may recall all the marked boxes for display, ie all the boxes isolating that marked cell from each frame (in the sequence) are superimposed into one image for inspection. Hence, the movement of the cell is reconstructed; measurements and calculations can then be made. This overlay image may also be permanently saved as one file.

The control panel for the electromechanical components, is integrated into the live screen. That is, when the live image is displayed, a control panel dialogue box appears (next to the live image) as well. The user uses the mouse to click on any button within the control panel to adjust any optical element before or during a measurement. For example, to extract a fluorescein angiogram, the user may click the following sequence on the control panel:

a. "PKH" to use green light (16, 17) to illuminate;
b. "FL" (23, 24) barrier to view fluorescein fluorescence;
c. "Magnify" to select the appropriate objective (28);
d. "Focus" to focus by moving the focusing doublet (21);
e. "FL" to use blue (16, 17) fluorescein excitation;
f. inject fluorescein;
g. "Trigger" or "Capture" for the image capture mode required.

The control panel provides selection of all a. excitation filters (16) in the filter wheel (17) in the illumination path (11);
b. barrier filters (23) in the filter wheel (24) in the imaging path (12);
c. speeds for the illumination Nipkow disc (18);
d. speeds for the imaging Nipkow disc (26);
e. objectives (28) for various magnifications.

Nipkow discs tracks are selected manually from the external X-Y-Z hardware control panel. The focusing lens group (21) is also controlled from this panel. In addition, all stepper motors can be "disarmed" for calibrations, manual adjustments and error-corrections. There is also a "RESET" button to re-initialize the system at any time.

To reduce the number of clicks required during a measurement, some selections may be combined into sequences; each sequence may then be activated by a single click. For example: instead of clicking to select a particular barrier filter (23), followed by another click to select the matching excitor filter (16), the two matched filters on the two wheels (17, 24) may be moved in one sequence when one button (say "FL") is clicked. Similarly, the two Nipkow disc assemblies (19, 27) may be coordinated to move in together such that the same patterns (ie the same tracks) are in the two paths.

(3) Higher level language (C++, Visual C++, Visual BASIC) programming of the algorithms for image capture and triggering control.

The aim is to image the capillary network during and throughout the arrival and subsequent filling of the network by the dye. However, the earliest advent will be at such low light levels and with such rapidity that user control of the start of image capture is impossible. Therefore, the imaging hardware—tube, camera, frame-grabber (FG), computer—must be electronically triggered to begin storing images just as the dye appears. Memory size prohibits continuous storage, from the moment of dye injection. Also, in order to capture the details of the progression of the dye (ie increase in intensity) as it fills the vasculature, the rate of image capture must be as fast as (electronically) possible. (The highest full-frame capture rate is 60 frames·s$^{-1}$)

The algorithm for triggering image capture is thus: the FG tests an incoming frame for changes in intensity. When the results of the calculations on a frame exceeds some preset threshold or background levels, the FG stops testing incoming frames and immediately begins to capture and store all incoming frames (into the temporary memory). Due to the memory space available in the present apparatus, a maximum of 180 frames can be captured and stored in any one capture sequence. The combination of capture speed and duration of capture is balanced to optimize the use of this memory space. For example: capture at 60 frames·s$^{-1}$ for 3 s, or, at 30 frames·s$^{-1}$ for 6 s, or, at 10 frames·s$^{-1}$ for 18 s. Properly optimized combinations should more than adequately cover the complete filing of the fundus. (Duration can be extended by increasing the temporary memory space on the frame-grabber board.)

To section the fundus, a specific routine in the software moves the focusing doublet (21) in 5–15 μm steps (ie change the focal plane of the doublet), capturing an image at the end of every step moved. A 3-dimensional image can then be reconstructed from the images of the layers.

Cell-tracking requires the invention to "stare" at a particular section of the retinal microvasculature, illuminate with the appropriate excitation waveband, and capture the fluorescence of the tagged blood cells as they enter and leave the field of view. Typically, such capture sequences require longer durations and slower frame speeds.

Figure 4:
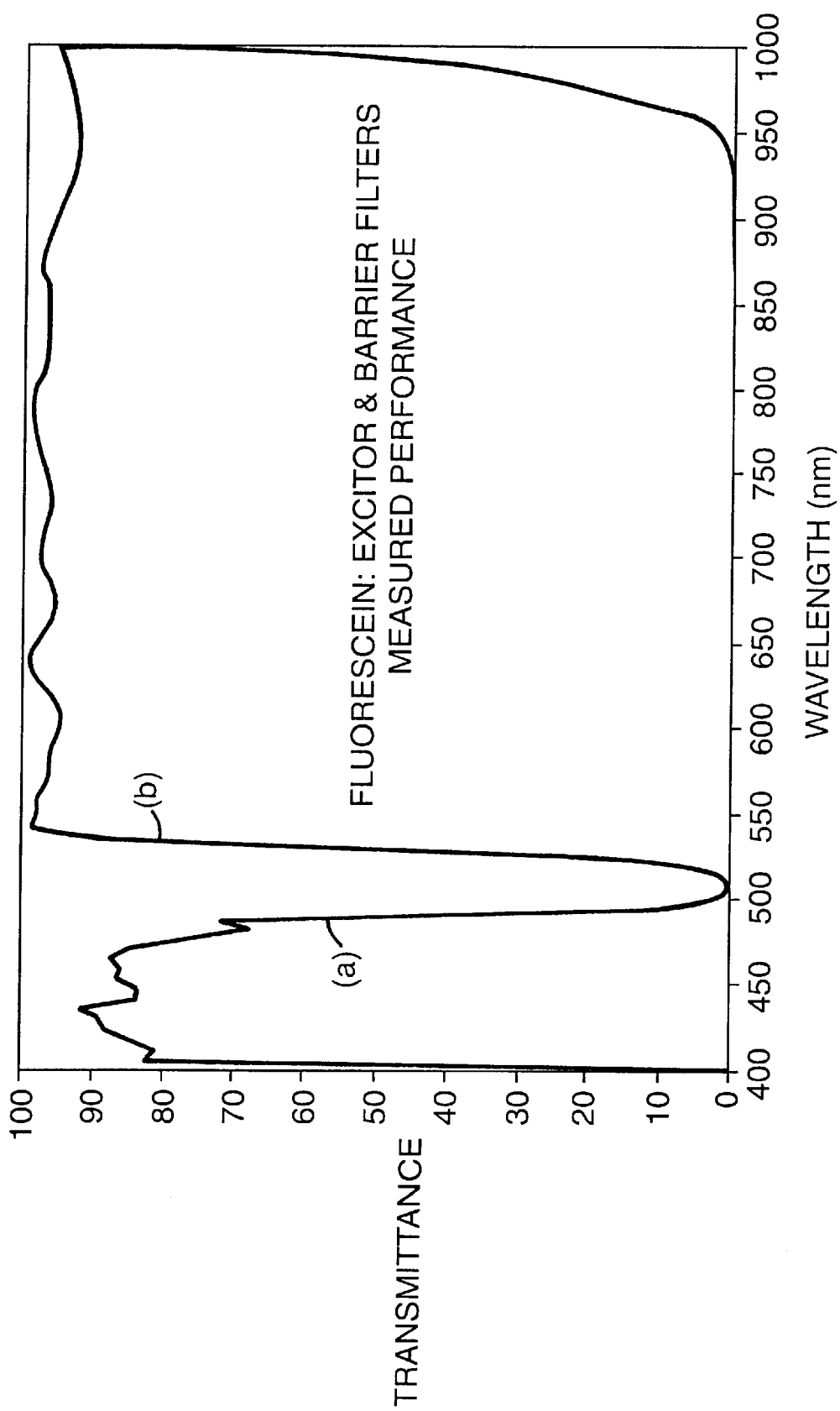
FIG. 4 shows a graph of the performance of fluorescein barrier and excitor filters.

FIG. 4 shows a measurement of transmittance against wavelength for excitor (a) and barrier (b) filters designed specifically for use with fluorescein. The excitor filter transmits at a level of 80% or more at a wavelength of between 410 and 475 nm. The transmittance falls steeply thereafter so that at 500 nm, it is just 5% and is nearly 0 at 510 nm. The transmittance of the barrier filter is essentially 0% at 500 nm and greater than 80% at wavelengths of 540 nm and longer. There is a steep increase in the transmittance of the barrier filter between 510 nm and 540 nm. This combination of filters is adapted for use with fluorescein which absorbs and is excited optimally by light of wavelength between 460 and 500 nm and subsequently fluoresces or emits optimally at wavelengths between 520 and 560 nm. The combination of filters is efficient due to the extremely small area of crossover around 500–510 nm and the steep cutoff and high transmittance of the filters above and below this crossover point. There is significant discrimination of illumination and fluorescence wavelengths, isolating them in their respective illumination and imaging paths.

Figure 5:
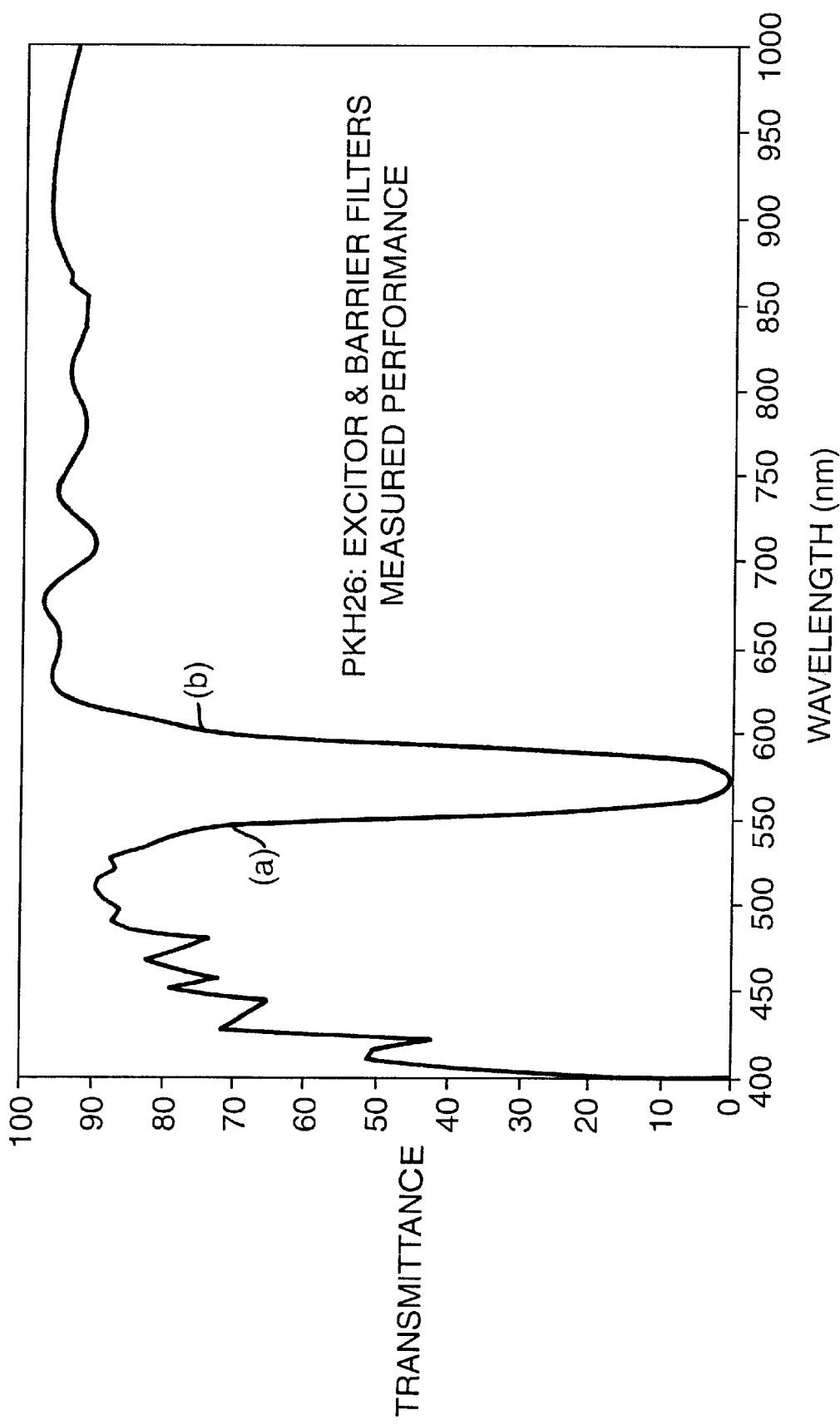
FIG. 5 shows a graph of the performance of PKH26 barrier and excitor filters.

FIG. 5 shows a measurement of transmittance against wavelength for PKH26 excitor (a) and barrier (b) filters. The excitor filter transmits at >70% in the 450–550 nm waveband and blocks light of wavelengths >590 nm. The barrier filter transmits at >70% for wavelengths longer than 605 nm and blocks light of wavelength <560 nm. The steep cutoff and rise in the respective excitor and barrier filters, the high transmittance and the small crossover about 570–580 nm, make them very specialised and efficient for PKH26. It should be noted that PKH26 has not been approved for use in humans.

Figure 6:
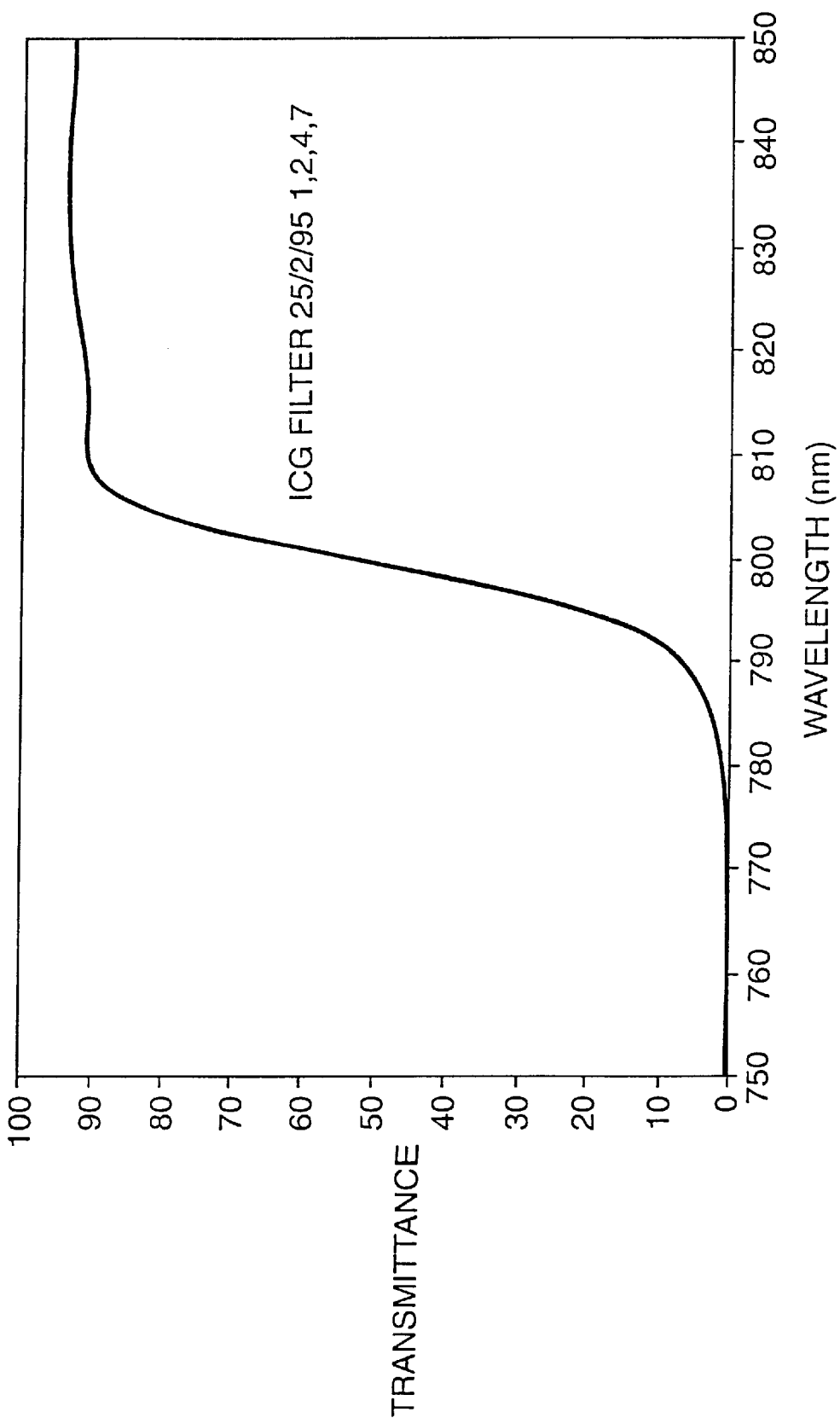
FIG. 6 shows a graph of the performance of ICG barrier filter.

FIG. 6 shows a measurement of transmittance against wavelength for a filter adapted for use with ICG fluorescence. Typically, ICG is excited using ~777 nm laser radiation. The barrier filter shown, substantially blocks all wavelengths <780 nm but transmits at >80% all wavelengths >810 nm. ICG fluorescence peaks around 830–840 nm although the spectral width is broad (750–880 nm). Hence, this barrier filter significantly optimizes the rejection of the illuminating laser wavelength (~777 nm), while transmitting the broadest possible ICG fluorescence spectrum.

The invention brings together several functions which are currently only available from different machines (usually operated by different personnel supporting the ophthalmologist), and a few capabilities not currently available in any device. It is based on the principles of confocal microscopy which produces high-contrast, shallow depth-of-focus imaging. Thus, the invention enables new techniques of viewing and analysing problems of pathological eyes at high magnification, in "real time" and if required, at high resolution. The invention makes available the multiple functions of viewing the fundus, analysing what is seen, and treating (photocoagulation) with a laser, if deemed necessary, in one device. This reduces the amount of time expended by the patient and the ophthalmologist, the costs in the maintenance of having and using different machines, and the additional supporting personnel required.

The full parts lists for the figures is:

- 10—general view
- 11—the illumination path
- 12—the imaging path
- 13—the treatment path
- 14—diode laser
- 15—optical switching assembly
- 16—excitation filters (varied according to sources used)
- 17—filter wheel
- 18—illumination Nipkow disc
- 19—motor assembly
- 20—cored mirror
- 21—focusing lens group
- 22—contact lens
- 23—imaging filters (varied according to sources used)
- 24—filter wheel
- 25—imaging lens group
- 26—imaging Nipkow disc
- 27—motor assembly for 26
- 28—microscope objectives
- 29—motor assembly
- 30—image intensifier with coupling relay lenses and CCD camera
- 31—laser mirror
- 32—illumination lens group #1
- 33—illumination lens group #2
- 34—mercury arc lamp
- 35—laser collimating lens group
- 36—light shaping diffuser
- 37—circular linear wedge neutral-density filter
- 38—laser collimating lens doublet
- 39—chopper blade
- 40—laser activation limit switch
- 41—X-Y axis table
- 42—z-axis table
- 43—base plate
- 44—rotary solenoid
- 45—tube-camera relay

What is claimed is:

1. Ophthalmologic examination apparatus comprising:
   a light source;
   illumination means for directing light from the source along an illumination path and into the fundus of an eye of a patient;
   imaging means for directing fluorescence from the fundus of the patient along an imaging path to enable an image of the eye to be viewed;
   wherein the illumination and imaging paths are arranged as a confocal microscope adapted to focus on the fundus of the eye.

2. Apparatus according to claim 1 wherein the confocal microscope has a depth of focus of about 50 μm or less.

3. Apparatus according to claim 2 wherein the confocal microscope has a depth of focus of about 30 μm or less.

4. Apparatus according to claim 1 wherein the illumination and imaging paths each pass through a Nipkow disc adapted in use to rotate at high speed.

5. Apparatus according to claim 4 comprising two Nipkow disks adapted separately to rotate at a speed of 2000–8000 rpm.

6. Apparatus according to claim 4 wherein rotation of the two discs is not synchronised.

7. Ophthalmologic examination apparatus comprising:
   a first source of visible light;
   a second source of non-visible light;
   illumination means for directing light along an illumination path and into a fundus of an eye of a patient; and
   imaging means for directing fluorescence from the fundus of the patient along an imaging path to enable an image of the fundus to be viewed;
   wherein the apparatus further comprises selector means comprising optical elements moveable between a first position in which light from the first source is directed along the illumination path and light from the second source is directed away from the illumination path, and a second position in which light from the second source is directed along the illumination path and light from the first source is directed away from the illumination path.

8. Apparatus according to claim 7 for simultaneous use of two dyes during the course of examination of an eye.

9. Apparatus according to claim 8 wherein the source of non-visible light is also adapted to treat neovascularization of the eye.

10. Apparatus according to claim 7 wherein the second source comprises a laser source of infra-red light whose intensity is variable between a low power adapted for viewing the eye and a high power adapted for treatment of neovascularization of the eye.

11. Ophthalmologic examination apparatus for examination of an eye of a patient using two or more fluorescent dyes, comprising
   illumination means for directing light along an illumination path into a fundus of an eye of the patient;
   imaging means for directing fluorescence from the eye along an imaging path for viewing an image of the ft'ndus of a patient;
   a first source of light adapted to excite a first dye;
   a second source of light adapted to excite a second dye;
   a first filter assembly in the illumination path adapted selectively to transmit light of a particular range of wavelengths into the eye that will excite the first or the second dye and a second filter assembly in the imaging path adapted selectively to transmit fluorescence from the first or the second dye along the imaging path; and
   selector means moveable between (i) a first position in which light from the first source is directed along the illumination path through the first filter assembly to excite a first dye and fluorescence from the eye is transmitted through the second filter assembly along the imaging path and (ii) a second position in which light from the second source is directed through the first filter assembly along the illumination path to excite a second dye and fluorescence from the eye is directed through the second filter assembly along the imaging path.

12. Apparatus according to claim 11 wherein the first and second sources of light are physically integrated into one and the same source, and the selector means is adapted to select the appropriate filter in the first filter assembly such that the appropriate ranges of excitation wavelengths are transmitted into the eye, and to select the appropriate filter in the second filter assembly in the imaging path such that fluorescence is transmitted along the imaging path.

13. Apparatus according to claim 11 wherein separate light sources are used each with an appropriate filter assembly specific to a particular fluorescent dye, and wherein in a first position of the selector means light from the first source passes through the first filter assembly along the illumination path and fluorescence passes through the second filter assembly along the imaging path, and, wherein in a second position of the selector means light from the second source passes through the first filter assembly along the illumination path and fluorescence through the second filter assembly along the imaging path.

14. Apparatus according to claim 11 wherein the light sources and selector means are arranged so that in use the operator has the option to switch back and forth between the sources and filters to match appropriate illumination to a specific dye being observed during the course of an eye examination.

15. Apparatus according to claim 11 wherein the first source generates light in the visible range and is adapted to excite the dye fluorescein.

16. Apparatus according to claim 11 wherein the second source generates laser light in the infra-red range and is adapted to excite the dye ICG.

17. Apparatus according to claim 11 wherein illumination is continuously transmitted through the first filter assembly along the illumination path thereby precluding the need for optically switching between sources.

18. Apparatus according to claim 11 further comprising a laser source of infra-red light for treatment of neovascularization by cauterization.

19. Apparatus according to claim 11 further comprising a laser source of any wavelength for treatment of neovascularization by photocoagulation.

20. A method of diagnosis of disease in an eye of a patient, comprising:
   providing in the ocular circulation of the patient:
      a first dye which fluoresces in response to illumination at a first predetermined wavelength; and
      a second dye which fluoresces in response to illumination at a second predetermined wavelength;
      wherein the first and second dyes fluoresce at different wavelengths;
   illuminating the fundus of the patient so as to excite the first dye at the first predetermined wavelength, and viewing an image of the eye by viewing fluorescence from the first dye; and subsequently illuminating the fundus of the patient so as to excite the second dye at the second predetermined wavelength, and viewing an image of the eye by viewing fluorescence from the second dye.

21. A method according to claim 20 comprising, when viewing an image from the first dye, using a filter which preferentially transmits fluorescence from the first dye.

22. A method according to claim 20 comprising, when viewing an image from the second dye, using a filter which preferentially transmits fluorescence from the second dye.

23. A method according to claim 20 wherein the first and second dyes are selected from the group consisting of Fluorescein, ICG and PKH26.

24. A method of examining an eye of a patient by:
   focusing on a thin layer of the fundus and storing an image of that thin layer;
   focusing on an axially adjacent or overlapping thin layer of the fundus and storing an image of that thin layer; and
   constructing a 3-dimensional image of the fundus or a portion of the fundus by combination or integration of the stored images.

25. A method according to claim 24 wherein the thin layers are less than about 30 μm deep.

26. A method according to claim 24 wherein focusing occturs in steps on adjacent or overlapping thin layers, storing images obtained of each thin layer, and an image in 3 dimensions is then constructed by aligning and combining the images.

27. A method of diagnosis of neovascularization in the choroidal and/or subretinal layers in an eye of a patient, wherein the first appearance of a dye in the eye, called "early filling", is captured at the microcirculatory level ie at the choriocapillaris level by the steps of:
   (a) identifying the plane of the microvasculature,
   (b) focusing on a layer slightly above the plane of the microvasculature so that the microvasculature plane will appear blurred and out of focus,
   (c) administering dye into the eye circulation, and
   (d) observing the identified layer,
   wherein neovascularization is expected to grow out of the plane of the microvasculature and into the focus of the apparatus and neovascular growth will stand out from a brightening but slower dye-staining and blurred background of the plane in the early filling phase.

28. A method of observation and optionally diagnosis of blood flow at the microcirculatory level in an eye of a patient, comprising
   (a) observing blood cells within normal or pathologically suspect areas of the fundus, and
   (b) estimating the blood flow velocity and/or the blood flow volume,
   wherein fluorescent marker dye is tagged to the blood cells.

29. A method according to claim 28 wherein blood cell motion is simulated by using fluorescein-filled microspheres which are biochemically inert in place of blood cells.

30. A filter assembly for use in fluorescence microscopy comprising:
   a first filter for fluorescein adapted to transmit substantially all light of wavelength between 410 and 475 nm and to block substantially transmission of all light of wavelength above 510 nm; and
   a second filter for fluorescein adapted to block substantially transmission of light of wavelength below 500 nm and to transmit substantially all light of wavelength above 540 nm.

31. A filter assembly for use in fluorescence microscopy comprising:
   a first filter for PKH26 adapted to transmit substantially all light or wavelength between 450–550 nm and to block substantially transmission of all light of wavelength above 590 nm; and
   a second filter for PKH26 adapted to block substantially transmission of all light of wavelength below 560 nm and to transmit substantially all light of wavelength above 605 nm.

32. A filter assembly for use in fluorescence microscopy comprising:
   a filter for ICG adapted to transmit substantially all light or wavelength longer than 810 nm and to block substantially transmission of all light of wavelength <780 nm.

33. Ophthalmologic examination apparatus comprising:
   illumination means for directing light along an illumination path and into an eye of a patient;
   imaging means for directing fluorescence from the fundus of the patient along an imaging path to enable an image of the fundus to be viewed;
   a first source of visible light; and
   a second source of non-visible light;
   wherein the apparatus further comprises selector means comprising optical elements moveable between a first position in which light from the first source is directed along the illumination path and light from the second source is directed away from the illumination path, and a second position in which light from the second source is directed along the illumination path and light from the first source is directed away from the illumination path.

34. Apparatus according to claim 33 for simultaneous use of two dyes during the course of examination of an eye.

35. Apparatus according to claim 34 wherein the source of non-visible light is also adapted to treat neovascularization of the eye.

36. Apparatus according to claim 35 wherein the second source comprises a laser source of infra-red light whose intensity is variable between a low power adapted for viewing the eye and a high power adapted for treatment of neovascularization of the eye.

37. Ophthalmologic examination apparatus for examination of an eye of a patient using two or more fluorescent dyes, comprising
   illumination means for directing light along an illumination path into the fundus of an eye of the patient;
   imaging means for directing fluorescence from the eye along an imaging path for viewing an image of the fundus of a patient;
   a first source of light adapted to excite a first dye;
   a second source of light adapted to excite a second dye;
   a first filter assembly in the illumination path adapted selectively to transmit light of a particular range of wavelengths into the eye that will excite the first or the second dye and a second filter assembly in the imaging path adapted selectively to transmit fluorescence from the first or the second dye along the imaging path; and,
   selector means moveable between a first position in which light from the first source is directed along the illumination path through the first filter assembly to excite a first dye and fluorescence from the eye is transmitted through the second filter assembly along the imaging path and a second position in which light from the second source is directed through the first filter assembly along the illumination path to excite a second dye and fluorescence from the eye is directed through the second filter assembly along the imaging path.

38. Apparatus according to claim 37 wherein the first and second sources of light are physically integrated or otherwise incorporated into one and the same source, and the selector means is adapted to select the appropriate filter in the first filter assembly such that the appropriate ranges of excitation wavelengths are transmitted into the eye, and to select the appropriate filter in the second filter assembly in the imaging path such that fluorescence is transmitted along the imaging path.

39. Apparatus according to claim 38 wherein separate light sources are used each with an appropriate filter assembly specific to a particular fluorescent dye, and wherein in a first position of the selector means light from the first source passes through the first filter assembly along the illumination path and fluorescence passes through the second filter assembly along the imaging path, and, wherein in a second position of the selector means light from the second source passes through the first filter assembly along the illumination path and fluorescence through the second filter assembly along the imaging path.

40. Apparatus according to claim 37 wherein the light sources and selector means are arranged so that in use the operator has the option to switch back and forth between the sources and filters to match appropriate illumination to a specific dye being observed during the course of an eye examination.

41. Apparatus according to claim 37 wherein the first source generates light in the visible range and is adapted to excite the dye fluorescein.

42. Apparatus according to claim 37 wherein the second source generates laser light in the infra-red range and is adapted to excite the dye ICG.

43. Apparatus according to claim 37 wherein illumination is continuously transmitted through the first filter assembly along the illumination path thereby precluding the need for optically switching between sources.

44. Apparatus according to claim 37 further comprising a laser source of infra-red light for treatment of neovascularization by cauterization.

45. Apparatus according to claim 37 further comprising a laser source of any wavelength for treatment of neovascularization by photocoagulation.

* * * * *